United States Patent
Berner et al.

(10) Patent No.: US 7,205,432 B2
(45) Date of Patent: Apr. 17, 2007

(54) PROCESS FOR THE PREPARATION OF ADAMANTANE DERIVATIVES

(75) Inventors: Mathias Berner, Helsinki (FI); Reijo Partanen, Kokkola (FI); Auli Salakka, Vantaa (FI); Pekka Somersalo, Espoo (FI)

(73) Assignee: Kemfine Oy, Helsinki (FI)

( * ) Notice: Subject to any disclaimer, the term of this patent is extended or adjusted under 35 U.S.C. 154(b) by 0 days.

(21) Appl. No.: 11/139,624

(22) Filed: May 31, 2005

(65) Prior Publication Data

US 2006/0270870 A1    Nov. 30, 2006

(51) Int. Cl.
*C07C 59/205*    (2006.01)
(52) U.S. Cl. ...................................................... 562/499
(58) Field of Classification Search ................ 562/499; 560/112
See application file for complete search history.

(56) References Cited

U.S. PATENT DOCUMENTS

2005/0090539 A1* 4/2005 Vu et al. .................... 514/412

* cited by examiner

*Primary Examiner*—Bernard Dentz
(74) *Attorney, Agent, or Firm*—Birch, Stewart, Kolasch & Birch, LLP

(57) ABSTRACT

The invention relates to a process for the preparation of 3-hydroxyadamantaneglyoxylic acid of the general formula (1)

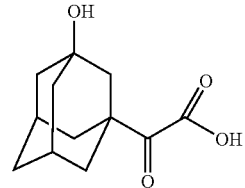

or a derivative or salt thereof. In the process, an 1-acyl derivative of adamantane having the formula (2):

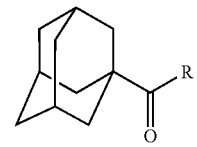

wherein R is a $C_1$–$C_5$ hydrocarbyl; $CH_2OH$; CHO; COOH, is contacted with an oxidant under oxidizing conditions leading to the 3-hydroxyadamantaneglyoxylic acid (1) or the derivative or salt thereof.

29 Claims, No Drawings

PROCESS FOR THE PREPARATION OF ADAMANTANE DERIVATIVES

FIELD OF THE INVENTION

The present invention relates to a process for the preparation of 3-hydroxyadamantaneglyoxylic acid of the general formula (1)

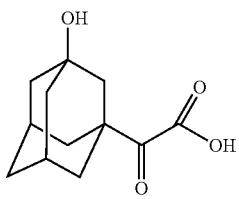

or a derivative or salt thereof.

BACKGROUND OF THE INVENTION

3-Hydroxyadamantaneglyoxylic acid (1) is an important intermediate for the synthesis of pharmacologically active dipeptidyl peptidase inhibitors, which inhibit cleavage of a peptide GLP-1 (7-36), responsible for stimulating insulin secretion and promotion of satiety and slowing of gastric emptying. PCT publication WO 2004/052850 discloses the following method of preparation of 3-hydroxyadamantaneglyoxylic acid (1) (Scheme 1):

SUMMARY OF THE INVENTION

The present invention provides a simple and direct method for the preparation of 3-hydroxyadamantaneglyoxylic acid (1) by contacting a 1-acyl derivative of adamantane having the formula (2):

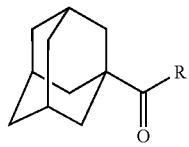

wherein R is a $C_1$–$C_5$ hydrocarbyl; $CH_2OH$; CHO; or COOH, with an oxidant under conditions leading to the 3-hydroxyadamantaneglyoxylic acid (1) or the derivative or salt thereof. The use of a 1-acyl derivative of adamantane as starting material avoids the difficulties encountered in the above described process according to the state of the art.

DETAILED DESCRIPTION OF THE INVENTION

As was said above, R of formula 2 may be a $C_1$–$C_5$ hydrocarbyl; $CH_2OH$; CHO; COOH; or CN. These groups R are known per se as carboxyl groups or groups that can be oxidized into carboxyl groups.

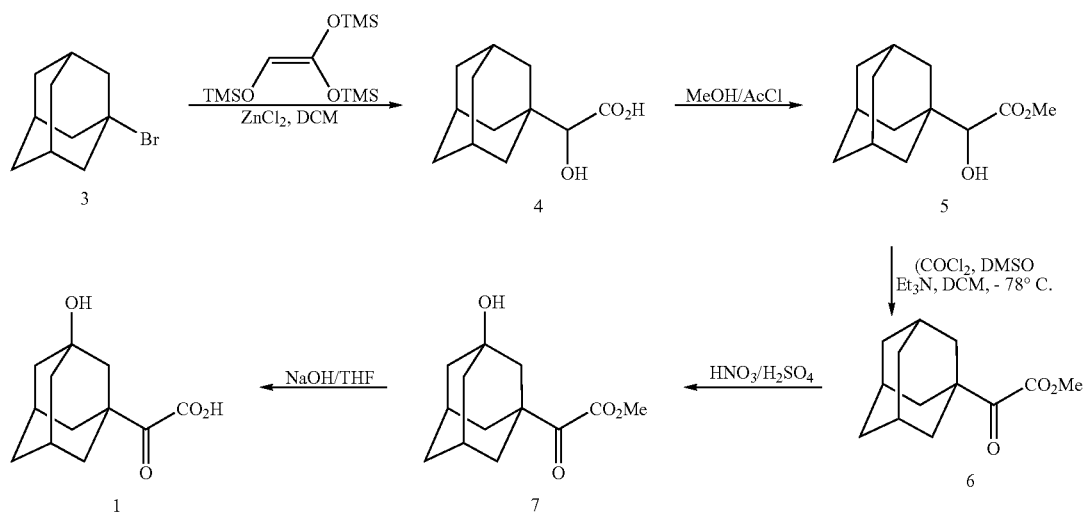

The method comprises a $ZnCl_2$-catalyzed coupling of 1-bromoadamantane (3) with tris(trimethylsiloxy)-ethylene in the environmentally difficult solvent dichloromethane to give the α-hydroxy acid derivative (4). Compound (4) was then esterified with a methanol/acetyl chloride solution to provide the α-hydroxy ester derivative (5). Swern oxidation of (5) at the technologically troublesome low temperature (keeping the internal temperature below −60° C.) with the assistance of hazardous oxalyl chloride yielded the glyoxylic ester (6). The ester (6) was then oxidized into the corresponding 3-hydroxy compound (7). Finally, hydrolysis of (7) with sodium hydroxide yielded the target molecule (1).

As can be seen, processes for the preparation of 3-hydroxyadamantaneglyoxylic acid have so far been laborious, hazardous and unpractical.

R of formula 2 is according to one embodiment of the invention a $C_1$–$C_5$ alkyl or a $C_1$–$C_5$ alkenyl. Methyl, ethyl and vinyl groups, for instance, readily form carboxyl upon oxidation. Preferably, R is $CH_3$, i.e. the starting compound 2 is 1-acetyl adamantane, whereby it is contacted with the oxidant under conditions oxidizing both the methyl group of the acetyl into a carboxyl group and the CH carbon 3 of the adamantyl skeleton into the corresponding carbinol. A process for the oxidation of the $CH_3$ of 1-acetyl adamantane is described in U.S. Pat. No. 3,325,478. However, the product was adamantaneglyoxylic acid and not the target compound 3-hydroxyadamantaneglyoxylic acid 1. The document thus teaches against the claimed invention.

According to a second embodiment of the invention, the 1-acyl derivative of adamantane is adamantaneglyoxylic acid, i.e. R of the above formula (2) is COOH, whereby it is contacted with the oxidant merely to oxidize the CH carbon number 3 of the adamantyl skeleton into the corresponding carbinol. The target compound (1) can thus be obtained by the direct oxidation of adamantaneglyoxylic acid.

The 1-acyl derivative of adamantane is typically contacted with the oxidant in solution. The nature and amount of the solvent must be such as to dissolve enough 1-acyl derivative of adamantane and oxidant to initiate and retain the desired oxidation reaction. One of the 1-acyl derivative of adamantane and the oxidant may be in one phase and the other in another, whereby the oxidation takes place at the surface between the phases.

Usually, these reagents are essentially dissolved in the same phase. Thereby, when the solvent of the solution has a dissolving power corresponding to that of water, the amount of the 1-acyl derivative of adamantane suitably is from 0.1 to 2 mol per litre of the solution. The order of contacting the derivative and the oxidant is not critical. According to a typical embodiment of the invention, the 1-acyl derivative of adamantane is first dissolved and then contacted with the oxidant. In order to achieve the right degree of oxidation, the oxidant and the solution component(s) are conveniently selected so that the oxidant is at least partly soluble in the solution component(s) and has essentially an analogous oxidizing effect on the 1-acyl derivative of adamantane as has potassium permanganate in a solution comprising the components water and alkali.

Applying the above mentioned preferred features of the claimed process, a simple and direct method for obtaining the target compound 1 is provided, in which the easily available or preparable 1-acyl derivatives of adamantane having the formula 2 are oxidised with an oxidant in a solvent in the presence of a base as depicted in Scheme 2.

Scheme 2

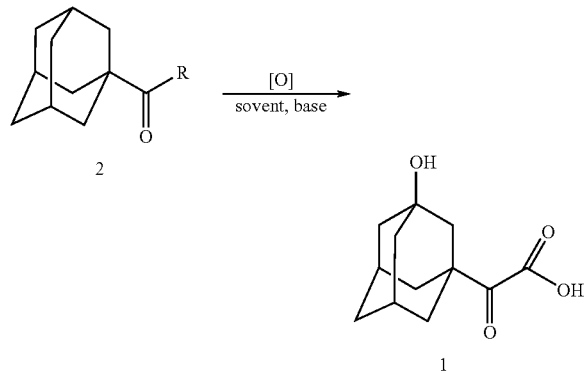

wherein R is as defined above and [O] is an oxidant.

The oxidant may be any oxidant capable of oxidizing 1-acyl derivatives of adamantane to the target compound 1. It can be selected from oxygen (both as diluted or undiluted $O_2$ and $O_3$), peroxides and peroxy acids, halogen compounds, chromium compounds, iron compounds, manganese compounds, lead compounds, redox resins, sulphur and selenium and their compounds, nitrogen compounds, as well as combinations of these. The oxidants may also be used together with oxidation catalysts such as the cobolt and nickel group metals.

The solution may as main component comprise a solvent selected e.g. from water, inert alcohols, carboxylic acids and esters thereof, chlorinated hydrocarbons, ketones, pyridine, and mixtures thereof. When selecting the solvent, partial or complete dissolution of the 1-acetyl derivative of adamantane may be the aim. The reaction can take place at the boundary surface between one phase comprising the derivative and another phase comprising the oxidant, whereby a phase transfer catalyst is recommended, see below. It may also take place by dissolving the derivative and the oxidant in the same solvent, whereby a more spontaneous reaction to the desired product takes place. The most preferred solvent is water.

Preferably, the oxidant is a permanganic acid salt and the solution comprises water as solvent and an alkali as oxidation catalyst and/or regulator. Most preferably, the permanganic acid salt is potassium or sodium permanganate. The oxidation proceeds especially smoothly if the molar ratio of the potassium permanganate to the 1-acyl derivative of adamantane is from 1.0 to 5.0 mol/mol, specifically from 2.0 to 4.0 mol/mol.

When oxidizing in one phase, the extent of the oxidation depends directly on the concentration of the oxidant in the solution containing the 1-acyl derivative of adamantane. Depending on its oxidation power, the concentration of the oxidant is or corresponds to 0.05–0.5 g/ml, preferably to 0.1–0.4 g/ml of $KMnO_4$ in the aqueous alkali solution.

According to one embodiment of the invention, the solution comprising water and an alkali also may comprise a water soluble organic solvent. Such an organic solvent may increase the solubility of the 1-acyl derivative of adamantane and therefore promote the oxidation. Typical useful water soluble solvents are e.g. inert (non-oxidizing) alcohols such as t-butanol, or pyridine.

Advantageously, the oxidation catalyzing and/or regulating alkali component of the solution comprising alkali and water is an alkali metal hydroxide or carbonate, an alkaline-earth metal hydroxide or carbonate, or ammonium hydroxide, or a mixture thereof. Most advantageously, it is NaOH, KOH or LiOH. When oxidizing in one aqueous phase, the molar ratio of alkali to 1-acyl derivative of adamantane is then typically from 0.1 to 0.6 mol/mol.

According to one version of the claimed invention, the solution comprises a phase transfer catalyst. Its purpose is to promote transfer of reactive matter from one phase to another and also function as a catalyst. In this invention, the phases may on the one hand be the 1-acyl derivative of adamantane undissolved and alone or dissolved in one solvent and on the other hand the oxidant dissolved in another solvent. In the embodiment of the invention which involves alkaline oxidation, such a phase transfer catalyst may, if basic, be used alone, or, otherwise, together with a base. Suitable phase transfer catalysts to be used together with bases are quaternary alkyl ammonium hydroxides such as tetrabutylammonium hydroxide or quaternary alkyl ammonium salts such as tetrabutylammonium bromide.

It has also been found that the 1-acyl derivative of adamantane preferably should be contacted with the oxidant at raised temperature, i.e. over room temperature (27° C.). A preferred temperature interval is 28 to 100° C., the most preferred being 30 to 70° C. Without limiting the scope of protection, the raised temperature most likely promotes the dissolution of the 1-acyl derivative of adamantane into the same medium as the oxidant which brings them together for more effective oxidation.

The 1-acyl derivative of adamantane should according to one embodiment of the invention be brought into contact with the oxidant gradually. Without limiting the scope of protection, it is believed that this gradual contacting has a regulating effect on the exothermic oxidation, giving a high yield of the target compound 1. A typical time span for the gradual contacting is from 0.25 h to 25 h, most preferably from 0.5 h to 10 h. See the examples below. Typically, after the gradual bringing into contact, the reaction mixture is mixed or kept standing for a certain period, which is usually 3 to 100 h.

Finally, the reaction mixture containing the oxidation product is worked up. This may include purification, acidification (pH<4), extraction, concentration and recrystallization. Optimization of these steps have lead to purities over 90%. See below. When preparing volatile derivatives of the 3-hydroxyadamantaneglyoxylic acid, recovery by distillation may be employed.

The preparation procedure of the 3-hydroxyadamanetaneglyoxylic acid (1) according to some typical embodiments of the invention is presented in the following examples.

EXAMPLE 1

30 g of 1-acetyladamantane was added to solution of 6.8 g of NaOH in 500 mL of water. The temperature of the suspension was increased to 40–50° C. and 80 g of potassium permanganate was added during a period of 1.5 h. The obtained mixture was stirred at 50–55° C. for 6 h and thereafter at room temperature 27° C. for 17 h followed by separation of the formed manganese dioxide precipitate by means of filtration. After the filtrate work-up that included acidification of filtrate, extractions with organic solvent and concentration of the combined organic phases, 28 g of partly crystallized material was obtained. Recrystallization of the material gave 13.6 g of the target 3-hydroxyadamantaneglyoxylic acid (1) as white crystalline solid with the purity 92.1% according to GC analysis of the corresponding methyl ester.

EXAMPLE 2

1.7 mL of NaOH 30% solution in water was diluted with 500 mL of water and 60 g of 1-acetyladamantane was added to that solution. Temperature of the suspension was increased to 35–40° C. and 144 g of potassium permanganate was added to the suspension during 0.5 h. The mixture was stirred at 35–40° C. for 25 h followed by manganese dioxide precipitate filtration. The filtrate work-up procedure consisting of acidification, extractions with organic solvent and concentration of the combined organic phases which resulted in 25.2 g of the target 3-hydroxyadamantaneglyoxylic acid (1) with purity 85.7% according to GC analysis of the corresponding methyl ester.

EXAMPLE 3

3.0 mL of NaOH 30% solutions in water was diluted with 120 mL of water. The solution was heated to 50° C. and 0.36 g of tetrabutylammonium bromide was added to the solution. Now 10 g of 1-acetyladamantane was added while stirring, followed by addition of 24.8 g of potassium permanganate during 4 h at 50–52° C. Stirring was continued for additional 4 h. The mixture was allowed to stay at room temperature for overnight and then manganese dioxide precipitate was filtered out. The filtrate work-up included acidification of filtrate, extraction and partial concentration of the combined organic phase. To the concentrated solution 10 mL of organic solvent was added and the mixture was kept at room temperature overnight. The formed crystals were filtered out, washed with solvent and dried to yield 4.7 g of the target 3-hydroxyadamantaneglyoxylic acid (1) with purity 96.4% according to GC analysis of the corresponding methyl ester.

EXAMPLE 4

10 g of 1-acetyladamantane was dissolved in a mixture of 55 mL of t-BuOH and 35 mL of water at 50° C. Then 1.0 mL of NaOH 30% water solution was added and temperature of the obtained solution was increased to 55–60° C. Then 35.5 g of potassium permanganate was added gradually during 5 h period at the temperature 55–65° C. Stirring was continued for 30 h at the same temperature 55–65° C. The mixture was then allowed to cool down to room temperature and manganese dioxide precipitate was filtered out. Now t-BuOH was evaporated from filtrate, the filtrate was acidified and extracted. Concentration of the extract gave 9.7 g of half solid residue containing 34.9% of 3-hydroxyadamantaneglyoxylic acid (1) and 58.1% of adamantaneglyoxylic acid according to GC analysis of the corresponding methyl esters. These compounds were separated in due course.

EXAMPLE 5

3.0 g 1-acetyladamantane was suspended in 40 mL of water. 4.0 mL of pyridine and 1.1 g of KOH was added and temperature of obtained suspension was increased to 55° C. Then 8.6 g of potassium permanganate was added gradually during 3 h at 55–60° C. and stirring was continued for an additional 3 h. The mixture was then allowed to stay 60 h at room temperature. Then, manganese dioxide precipitate was filtered out and the filtrate was acidified and extracted. Concentration of the extract gave 3.7 g of partly crystallized material containing mainly 3-hydroxyadamantaneglyoxylic acid (1).

EXAMPLE 6

2.8 mL of NaOH 30% solution in water was diluted with 30 mL of water. The solution was heated to 55° C. and 3.0 g of adamantaneglyoxylic acid was dissolved therein. Then 3.3 g of potassium permanganate was added gradually during 2 h and stirring of obtained the obtained mixture was continued for 9 h at 55–60° C. The mixture was allowed to stay at room temperature for overnight. Then manganese dioxide precipitate was filtered out and the filtrate work-up procedure consisting of acidification, extraction with organic solvent and concentration of the combined organic phases resulted in 2.5 g of the target 3-hydroxyadamantaneglyoxylic acid (1) with purity 68.9% according to GC analysis of the corresponding methyl ester.

The invention claimed is:

1. A process for the preparation of 3-hydroxyadamantaneglyoxylic acid of the general formula (1)

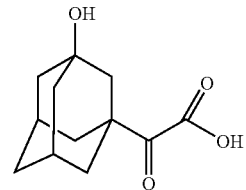

1 or a derivative or salt thereof, characterized in that a 1-acyl derivative of adamantane having the formula (2):

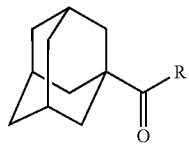

2 wherein R is a $C_1$–$C_5$ hydrocarbyl; $CH_2OH$; CHO; or COOH, is contacted with an oxidant under oxidizing conditions leading to the 3-hydroxyadamantaneglyoxylic acid (1) or the derivative or salt thereof.

2. A process according to claim 1, characterized in that the 1-acyl derivative of adamantane is 1-acetyl adamantane (R is $CH_3$), whereby it is contacted with the oxidant under conditions oxidizing the methyl group of the 1-acetyl into a carboxylic group and the CH carbon 3 of the adamantyl skeleton into a carbinol.

3. A process according to claim 1, characterized in that the 1-acyl derivative of adamantane is adamantaneglyoxylic acid (R is COOH), whereby it is contacted with the oxidant under conditions oxidizing the CH carbon 3 of the adamantyl skeleton into a carbinol.

4. A process according to claim 1, characterized in that the 1-acyl derivative of adamantane is contacted with the oxidant in solution.

5. A process according to claim 4, characterized in that the amount of the 1-acyl derivative of adamantane is from 0.1 to 2 mol per litre of the solution.

6. A process according to claim 4, characterized in that the 1-acyl derivative of adamantane is first dissolved and then contacted with the oxidant.

7. A process according to claim 6, characterized in that the oxidant and the solution component(s) are selected so that the oxidant is at least partly soluble in the solution and has essentially the same oxidizing effect on the 1-acyl derivative of adamantane as potassium permanganate in a solution comprising water and an alkali.

8. A process according to claim 7, characterized in that the oxidant is selected from oxygen (diluted or undiluted $O_2$, $O_3$), peroxides and peroxy acids, halogen compounds, chromium compounds, iron compounds, manganese compounds, lead compounds, redox resins, sulphur and its compounds, selenium and its compounds, nitrogen compounds, as well as combinations of these.

9. A process according to claim 7, characterized in that the solution comprises as said component a solvent selected from water, inert alcohols, inert carboxylic acids and esters thereof, inert chlorinated hydrocarbons, inert ketones and pyridine, or a mixture thereof.

10. A process according to claim 9, characterized in that the oxidant is a permanganic acid salt and the solution comprises as said components water and an alkali.

11. A process according to claim 10, characterized in that the permanganic acid salt is potassium or sodium permanganate.

12. A process according to claim 11, characterized in that the molar ratio of the potassium permanganate to the 1-acyl derivative of adamantane is 1.0 to 5.0 mol/mol.

13. A process according to claim 12, characterized in that the molar ratio of the potassium permanganate to the 1-acyl derivative of adamantane is 2.0 to 4.0 mol/mol.

14. A process according to claim 10, characterized in that the solution comprising water and an alkali also comprises an organic solvent.

15. A process according to claim 14, characterized in that the organic solvent is an inert alcohol and/or pyridine.

16. A process according to claim 10, characterized in that the alkali is an alkali metal hydroxide or carbonate, an alkaline-earth metal hydroxide or carbonate, or ammonium hydroxide or a mixture thereof.

17. A process according to claim 16, characterized in that the alkali is NaOH, KOH or LiOH.

18. A process according to claim 16, characterized in that the molar ratio of alkali to 1-acyl derivative of adamantane is 0.05 to 5.0 mol/mol.

19. A process according to claim 18, characterized in that the molar ratio of alkali to 1-acyl derivative of adamantane is 0.1 to 0.6 mol/mol.

20. A process according to claim 4, characterized in that the solution comprises a phase transfer catalyst.

21. A process according to claim 20, characterized in that the phase transfer catalyst is a quaternary alkyl ammonium hydroxide or a quaternary alkyl ammonium salt.

22. A process according to claim 1, characterized in that the 1-acyl derivative of adamantane is contacted with the oxidant at a raised temperature.

23. A process according to claim 22, characterized in that the raised temperature is from 28 to 100° C.

24. A process according to claim 23, characterized in that the raised temperature is from 30 to 70° C.

25. A process according to claim 1, characterized in that the 1-acyl derivative of adamantane is brought into contact with the oxidant gradually.

26. A process according to claim 25, characterized in that the gradual contacting takes place during a time span selected from 0.25 h to 25 h.

27. A process according to claim 26, characterized in that the gradual contacting takes place during a time span selected from 0.5 h to 10 h.

28. A process according to claim 25, characterized in that after the gradual contacting, the 1-acyl derivative of adamantane is kept in contact with the oxidant.

29. A process according to claim 28, characterized in that the 1-acyl derivative of adamantane is kept in contact with the oxidant for a time span selected from 3 to 100 h.

* * * * *